(12) United States Patent
Chan

(10) Patent No.: US 11,517,351 B2
(45) Date of Patent: Dec. 6, 2022

(54) EXTERNAL FIXATION DEVICES FOR POSTERIOR PELVIC COMPRESSION AND METHODS OF USE

(71) Applicant: Daniel Chan, Macon, GA (US)

(72) Inventor: Daniel Chan, Macon, GA (US)

(*) Notice: Subject to any disclaimer, the term of this patent is extended or adjusted under 35 U.S.C. 154(b) by 138 days.

(21) Appl. No.: 16/972,347

(22) PCT Filed: Jun. 4, 2019

(86) PCT No.: PCT/US2019/035461
§ 371 (c)(1),
(2) Date: Dec. 4, 2020

(87) PCT Pub. No.: WO2019/236630
PCT Pub. Date: Dec. 12, 2019

(65) Prior Publication Data
US 2021/0236171 A1 Aug. 5, 2021

Related U.S. Application Data

(60) Provisional application No. 62/680,254, filed on Jun. 4, 2018.

(51) Int. Cl.
*A61B 17/66* (2006.01)
*A61B 17/64* (2006.01)
(Continued)

(52) U.S. Cl.
CPC ........ *A61B 17/6433* (2013.01); *A61B 17/645* (2013.01); *A61B 17/6466* (2013.01);
(Continued)

(58) Field of Classification Search
CPC .............. A61B 17/6433; A61B 17/645; A61B 17/6466; A61B 17/6441
See application file for complete search history.

(56) References Cited

U.S. PATENT DOCUMENTS 3,865,105 A * 2/1975 Lode .................. A61B 17/7049
606/54
4,138,168 A 2/1979 Herlitzek
(Continued)

FOREIGN PATENT DOCUMENTS

CH 685532 A5 * 8/1995 ......... A61B 17/6433
DE 102010032465 A1 * 2/2012 ............. A61B 17/66

OTHER PUBLICATIONS

International Search Report and Written Opinion issued by the International Searching Authority (ISA/US) in PCT Application No. PCT/US2019/035461 dated Aug. 28, 2019. 16 pages.
(Continued)

*Primary Examiner* — Jan Christopher L Merene
(74) *Attorney, Agent, or Firm* — Meunier Carlin & Curfman LLC

(57) ABSTRACT

Various implementations include an external fixation device for posterior pelvic compression that allows a pin engaged into one iliac bone to be pivoted relative to the pin engaged into the other iliac bone, allowing compression of the iliac bones toward each other and the interposed sacrum and for the relative positions of the pins to be held fixed relative to each other after the compression is set. The pin to be pivoted is engaged into the iliac bone closest to the source of the injury. And, the pins and bars of the fixation device are anteriorly coupled together, which gives the patient greater transportability, as well as maintenance of reduction that will assist in the definitive surgical intervention.

19 Claims, 4 Drawing Sheets

(51) Int. Cl.
  *A61B 17/00* (2006.01)
  *A61B 17/56* (2006.01)
(52) U.S. Cl.
  CPC .... *A61B 17/66* (2013.01); *A61B 2017/00367* (2013.01); *A61B 2017/564* (2013.01)

(56) References Cited

U.S. PATENT DOCUMENTS

| | | | |
|---|---|---|---|
| 4,361,144 A | 11/1982 | Slatis | |
| 5,219,349 A * | 6/1993 | Krag | A61B 17/7077 606/53 |
| 5,350,378 A * | 9/1994 | Cole | A61B 17/6433 606/57 |
| 5,443,464 A * | 8/1995 | Russell | A61B 17/6483 606/56 |
| 5,676,664 A * | 10/1997 | Allard | A61B 17/66 606/57 |
| 6,491,694 B1 | 12/2002 | Orsak | |
| 6,702,814 B2 | 3/2004 | Walulik et al. | |
| 9,883,890 B2 | 2/2018 | Miller et al. | |
| 2007/0038217 A1 | 2/2007 | Brown et al. | |
| 2010/0198267 A1 | 8/2010 | Vaidya | |

OTHER PUBLICATIONS

Burgess, Andrew R., et al. "Pelvic ring disruptions: effective classification system and treatment protocols." Journal of Trauma and Acute Care Surgery 30.7 (1990): 848-856.

Dalal, Samir A., et al. "Pelvic fracture in multiple trauma: classification by mechanism is key to pattern of organ injury, resuscitative requirements, and outcome." The Journal of trauma 29.7 (1989): 981-1000.

Dujardin, F. H., et al. "Long-term functional prognosis of posterior injuries in high-energy pelvic disruption." Journal of orthopaedic trauma 12.3 (1998): 145-150.

Holstein, Joerg H., et al. "What are predictors of mortality in patients with pelvic fractures?." Clinical Orthopaedics and Related Research® 470.8 (2012): 2090-2097.

Jowett, A. J. L., and G. W. Bowyer. "Pressure characteristics of pelvic binders." Injury 38.1 (2007): 118-121.

Krieg, James C., et al. "Emergent stabilization of pelvic ring injuries by controlled circumferential compression: a clinical trial." Journal of Trauma and Acute Care Surgery 59.3 (2005): 659-664.

Magnussen, Robert A., et al. "Predicting blood loss in isolated pelvic and acetabular high-energy trauma." Journal of orthopaedic trauma 21.9 (2007): 603-607.

Mullis, Brian H., and H. Claude Sagi. "Minimum 1-year follow-up for patients with vertical shear sacroiliac joint dislocations treated with iliosacral screws: does joint ankylosis or anatomic reduction contribute to functional outcome?." Journal of orthopaedic trauma 22.5 (2008): 293-298.

Rockwood and Green's Fractures in Adults, 8th Ed. Chapter 46, 2014, p. 1806.

Routt Jr, Chip ML, et al. "Circumferential pelvic antishock sheeting: a temporary resuscitation aid." Journal of orthopaedic trauma 16.1 (2002): 45-48.

Sellei, Richard Martin, et al. "Can a modified anterior external fixator provide posterior compression of AP compression type III pelvic injuries?." Clinical Orthopaedics and Related Research® 471.9 (2013): 2862-2868.

Tornetta, Paul, and Joel M. Matta. "Outcome of operatively treated unstable posterior pelvic ring disruptions." Clinical Orthopaedics and Related Research® 329 (1996): 186-193.

Wong, Yon-Cheong, et al. "Mortality after successful transcatheter arterial embolization in patients with unstable pelvic fractures: rate of blood transfusion as a predictive factor." Journal of Trauma and Acute Care Surgery 49.1 (2000): 71-75.

\* cited by examiner

EXTERNAL FIXATION DEVICES FOR POSTERIOR PELVIC COMPRESSION AND METHODS OF USE

CROSS REFERENCE TO RELATED APPLICATIONS

This application is a national stage application filed under 35 U.S.C. § 371 of PCT/US2019/035461 filed Jun. 4, 2019, which claims priority to U.S. Patent Application No. 62/680,254, entitled "External Fixation Devices for Posterior Pelvic Compression and Methods of Use," filed Jun. 4, 2018, the contents of which are herein incorporated by reference in their entireties.

BACKGROUND

Pelvic ring injuries can be associated with significant blood loss due to instability in the posterior ring of the pelvis. In scenarios such as hemodynamic instability, current initial treatment includes: 1) a pelvic binder or circumferential sheet placement to limit the displacement of the pelvis fragments and tamponade the bleeding; or 2) emergent operative intervention to explore the abdomen and/or perform pelvic packing to control the bleeding. In these operative situations, an external fixator is often placed on the anterior ring of the pelvis to offer some, but limited, stability to the unstable pelvic fracture. Pelvic binders can only be used for a limited length of time due to skin tolerance, or the binder may be on top of the surgical incisions or an open abdominal wound. In addition, external fixators may be disposed anteriorly of the patient, but no forces are enforced to the back of the pelvis through these fixators.

Thus, in light of these limitations, improved fixation devices and methods of use are needed.

BRIEF SUMMARY

Various implementations include an external fixation device for posterior pelvic compression. The device includes a first pin, a second pin, a first bar, a second bar, first and second fixed clamps, a distractor, and a hinge clamp. The first pin has a first end and a second end and an axis extending through the first and second ends. The first end is disposable into a first iliac wing of a patient. The second pin has a first end and a second end and axis extending through the first and second ends of the second pin. The first end of the second pin is disposable into a second iliac wing of the patient. The first bar has a first end and a second end and an axis extending between the first and second ends of the first bar. The first bar is coupled to the first pin at a first region of the first pin and adjacent the first end of the first bar, and the first bar is coupled to the second pin at a second region of the second pin and adjacent the second end of the first bar. The second bar has a first end and a second end and an axis extending between the first and second ends of the second bar. The second bar is coupled to the first pin at a third region of the first pin and adjacent the first end of the second bar, and the second bar is coupled to the second pin at a fourth region of the second pin and adjacent the second end of the second bar. The third region is disposed between the first end of the first pin and the first region, and the fourth region is disposed between the first end of the second pin and the second region. The first fixed clamp couples the first bar and the second pin at the second region, and the second fixed clamp couples the second bar and the second pin at the fourth region. The distractor couples the first bar and the first pin and is coupled to the first pin at the first region of the first pin. The hinge clamp couples the second bar and the first pin at the third region. The third region is between the first region and the first end of the first pin. The hinge clamp is rotatable about a hinge axis, wherein the hinge axis is transverse to a first plane that includes the axis of the first pin and a second plane that includes the axis of the first bar such that an angle between the axis of the first pin and the axis of the second bar is able to change. Actuation of the distractor urges the first region of the first pin along the axis of the first bar, which causes the first pin to pivot about the hinge axis of the hinge clamp.

In some implementations, the distractor comprises an actuation bar having an actuation bar axis extending through the actuation bar, an actuation housing, an actuation device, a first distractor clamp, a second distractor clamp, a third distractor clamp, and a fourth distractor clamp. The actuation device is operable for causing the actuation bar to slide along the actuation bar axis relative to the housing. The first distractor clamp is fixedly coupled to the first bar. The second distractor clamp is fixedly coupled to the actuation bar and slidably coupled to the first bar between the third distractor clamp and the fourth distractor clamp. The third distractor clamp is coupled to the first pin and slidably coupled to the first bar. And, the fourth distractor clamp is fixedly coupled to the actuation housing and slidably coupled to the first bar between the second distractor clamp and the first distractor clamp. When the actuation device is actuated, a portion of the actuation bar that is coupled to the third distractor clamp slides along the actuation bar axis away from the actuation housing, the fourth distractor clamp is urged into abutment with the first distractor clamp, and the second distractor clamp urges the third distractor clamp and the second end of the first pin in a direction away from the actuation housing, and the first end of the first pin is moved toward the first end of the second pin.

In some implementations, the actuation bar defines axially spaced notches, and the actuation device comprises a trigger that is alternately pulled and released to engage the notches upon actuation of the actuation device to push the actuation bar along the actuation bar axis.

In some implementations, the actuation device comprises threads that extend radially inwardly of a channel defined in the housing, and the actuation bar defines threads that extend radially outwardly along at least a portion thereof. Actuation of the actuation device comprises rotating the actuation bar about the actuation bar axis to move the third distractor clamp away from the actuation housing.

In some implementations, the actuation bar axis is parallel to an axis of the first bar.

In some implementations, the distractor is fixedly coupled to the first region of the first pin.

In some implementations, the hinge clamp comprises a pin portion and a bar portion. The pin portion and the bar portion are coupled together via a rotational coupling that extends between the pin portion and the bar portion. And, the pin portion and the bar portion are independently rotatable relative to each other about an axis of the rotational coupling. The pin portion defines a pin opening that receives the first pin, and the bar portion defines a bar opening that receives the second bar.

In some implementations, the rotational coupling comprises a shaft, and the hinge clamp further includes at least one washer disposed between facing surfaces of the pin and bar portions. The shaft extends through an opening defined in the at least one washer.

In some implementations, the at least one washer includes a first washer and a second washer, and the hinge clamp further includes a spacer disposed between the first and second washers.

In some implementations, the spacer comprises an integrally formed protrusion that extends radially outwardly from an outer surface of the shaft.

In some implementations, the spacer comprises a separately formed disc disposed around the shaft that maintains a gap between the washers.

In some implementations, the shaft comprises a threaded portion adjacent a first end of the shaft, and at least a portion of the threaded portion extends distally of one of the bar portion or the pin portion. The hinge clamp further comprises a nut that threadingly engages the threaded portion to urge the pin and bar portions axially toward or away from each other.

In some implementations, the shaft includes a head adjacent a second end of the shaft, and the head is disposed adjacent a distal surface of the other of the pin portion or the bar portion.

In some implementations, the threaded portion is a first threaded portion and the nut is a first nut. The shaft comprises a second threaded portion adjacent a second end of the shaft, and at least a portion of the second threaded portion extends distally of the other of the pin or bar portion. The hinge clamp comprises a second nut that threadingly engages the threaded portion to urge the pin and bar portions axially toward or away from each other.

In some implementations, the rotational coupling comprises a pair of annular races and a plurality of ball bearings disposed between the races.

In some implementations, the hinge clamp comprises a pin portion and a bar portion movably coupled together by a universal joint. The pin portion defines a pin opening that receives the first pin, and the bar portion defines a bar opening that receives the second bar.

In some implementations, the hinge clamp comprises a pin portion and bar portion rotatably coupled by a ball and socket joint. The pin portion defines a pin opening for fixedly receiving the first pin, and the bar portion defines a bar opening for fixedly receiving the second bar. The device further includes a third fixed clamp disposed between the first end of the second bar and the hinge clamp. The third fixed clamp prevents movement of the hinge clamp along the axis of the second bar.

In some implementations, the device further includes a third bar. The third bar is fixedly coupled to the first bar and the second bar. The third bar prevents the axes of the first and second bars from moving out of a plane that includes the axes of the first and second bars.

In some implementations, the first ends of the first and second pins are threaded.

In some implementations, the first and second pins are Schanz pins.

In some implementations, an elongated sleeve is disposed around and coupled to at least a portion of the first pin adjacent the second end of the first pin, and the third distractor clamp is fixedly coupled to the elongated sleeve.

In some implementations, the elongated sleeve is slidably coupled to the first pin.

In some implementations, the elongated sleeve defines a slot extending radially through a wall of the sleeve. The slot has an axis that is parallel to the axis of the first pin. The further comprises a fastener that extends through the slot and engages the first pin. The slot limits a length that the sleeve can slide relative to the first pin.

Various implementations include a method of assembling an external fixation device for applying pelvic compression. The method includes: (1) engaging a first end of a first pin into a first iliac wing of a patient, the first pin having a second end opposite the first end and an axis extending through the first and second ends; (2) engaging a first end of a second pin into a second iliac wing of a patient, the second pin having a second end opposite the first end of the second pin and an axis extending through the first and second ends of the second pin; (3) coupling a first bar to the second pin, wherein the first bar includes a first end and a second end and an axis extending between the first and second ends of the first bar, wherein the first bar is fixedly coupled to the second pin at a second region of the second pin and adjacent the second end of the second bar; (4) coupling a distractor to the first bar and the first pin, the distractor being coupled to a first region of the first pin and to the first bar adjacent the first end of the first bar, wherein the distractor is actuatable for moving the first region of the first bar; (5) coupling a second bar to the first pin and the second pin, the second bar having a first end and a second end and an axis extending between the first and second ends of the second bar, wherein the second bar is hingedly coupled to the first pin at a third region of the first pin and adjacent the first end of the second bar, and the second bar is fixedly coupled to the second pin at a fourth region of the second pin and adjacent the second end of the second bar, and wherein the third region is disposed between the first end of the first pin and the first region, and the fourth region is disposed between the first end of the second pin and the second region; and (6) actuating the distractor to cause the first region of the first pin to move along the axis of the first bar, which causes the first pin to pivot about the hinged coupling relative to the second bar.

In some implementations, the distractor is fixedly coupled to the first region of the first pin.

In some implementations, actuating the distractor to cause the first region of the first pin to move away from the second pin along the axis of the first bar causes compression of the first iliac wing toward the second iliac wing.

In some implementations, the second bar is hingedly coupled to the first pin with a hinge clamp. The hinge clamp is rotatable about a hinge axis, and the hinge axis is transverse to a first plane that includes the axis of the first pin and a second plane that includes the axis of the first bar such that an angle between the axis of the first pin and the axis of the second bar is able to change.

In some implementations, the hinge clamp comprises a pin portion and bar portion rotatably coupled by a ball and socket joint. The pin portion defines a pin opening for fixedly receiving the first pin, and the bar portion defines a bar opening for fixedly receiving the second bar. The device further includes a third fixed clamp disposed between the first end of the second bar and the hinge clamp. The third fixed clamp prevents movement of the hinge clamp along the axis of the second bar.

In some implementations, the hinge clamp comprises a pin portion defining a pin opening for receiving a pin of the external fixation device, a bar portion defining a bar opening for receiving a bar of the external fixation device, and a rotational coupling having a rotational axis. The pin portion and the bar portion are coupled together via the rotational coupling. The rotational coupling extends between facing surfaces of the pin portion and the bar portion. The pin portion and the bar portion have a single rotational degree of freedom about the rotational axis such that a first plane that includes a pin axis extending through the pin opening and a second plane that includes a bar axis extending through the bar opening remain parallel during relative rotation of the pin portion and bar portion about the rotational axis of the rotational coupling.

Various implementations include a hinge clamp for a posterior pelvic compression external fixation device. The hinge clamp includes a pin portion defining a pin opening for receiving a pin of the external fixation device, a bar portion defining a bar opening for receiving a bar of the external fixation device, and a rotational coupling having a rotational axis. The pin portion and the bar portion are coupled together via the rotational coupling. The rotational coupling extends between facing surfaces of the pin portion and the bar portion. The pin portion and the bar portion have a single rotational degree of freedom about the rotational axis such that a first plane that includes a pin axis extending through the pin opening and a second plane that includes a bar axis extending through the bar opening remain parallel during relative rotation of the pin portion and bar portion about the rotational axis of the rotational coupling.

In some implementations, the rotational coupling comprises a shaft, and the hinge clamp further comprises at least one washer disposed between facing surfaces of the pin and bar portions. The shaft extends through an opening defined in the washer.

In some implementations, the at least one washer includes a first washer and a second washer, and the hinge clamp further includes a spacer disposed between the first and second washers.

In some implementations, the spacer comprises an integrally formed radially outward protrusion that extends from an outer surface of the shaft.

In some implementations, the spacer comprises a separately formed disc disposed around the shaft that maintains a gap between the washers.

In some implementations, the shaft comprises a threaded portion adjacent a first end of the shaft, and at least a portion of the threaded portion extends distally of one of the bar portion or the pin portion. The hinge clamp further comprises a nut that threadingly engages the threaded portion to urge the pin and bar portions axially toward or away from each other.

In some implementations, the shaft includes a head adjacent a second end of the shaft. The head is disposed adjacent a distal surface of the other of the pin portion or the bar portion.

In some implementations, the threaded portion is a first threaded portion and the nut is a first nut. The shaft comprises a second threaded portion adjacent a second end of the shaft, and at least a portion of the second threaded portion extends distally of the other of the pin or bar portion. The hinge clamp comprises a second nut that threadingly engages the threaded portion to urge the pin and bar portions axially toward or away from each other.

In some implementations, first and second ends of the shaft are embedded within the pin portion and the bar portion, respectively.

In some implementations, the rotational coupling comprises a pair of annular races and a plurality of ball bearings disposed between the races.

DETAILED DESCRIPTION

Various implementations include an external fixation device for posterior pelvic compression that allows a pin engaged into one iliac bone to be pivoted relative to the pin engaged into the other iliac bone, allowing reduction of the sacral-iliac (SI) joint via compression of the iliac bones toward each other and against the sacrum and for the relative positions of the pins to be held fixed relative to each other after the compression is set. The pin to be pivoted is engaged into the iliac bone closest to the source of the injury. In addition, the pins and bars of the fixation device are anteriorly coupled together, which allows for easier transportability of the patient, as well as maintenance of reduction that will assist in the definitive surgical intervention. By maintaining the reduction until a definitive surgical procedure is performed, bleeding and pain are decreased, and the next stage of surgery is facilitated by maintaining the SI joint in proper alignment, which may result in smaller incisions, less blood loss, and less operative/anesthesia time.

Figure 1:
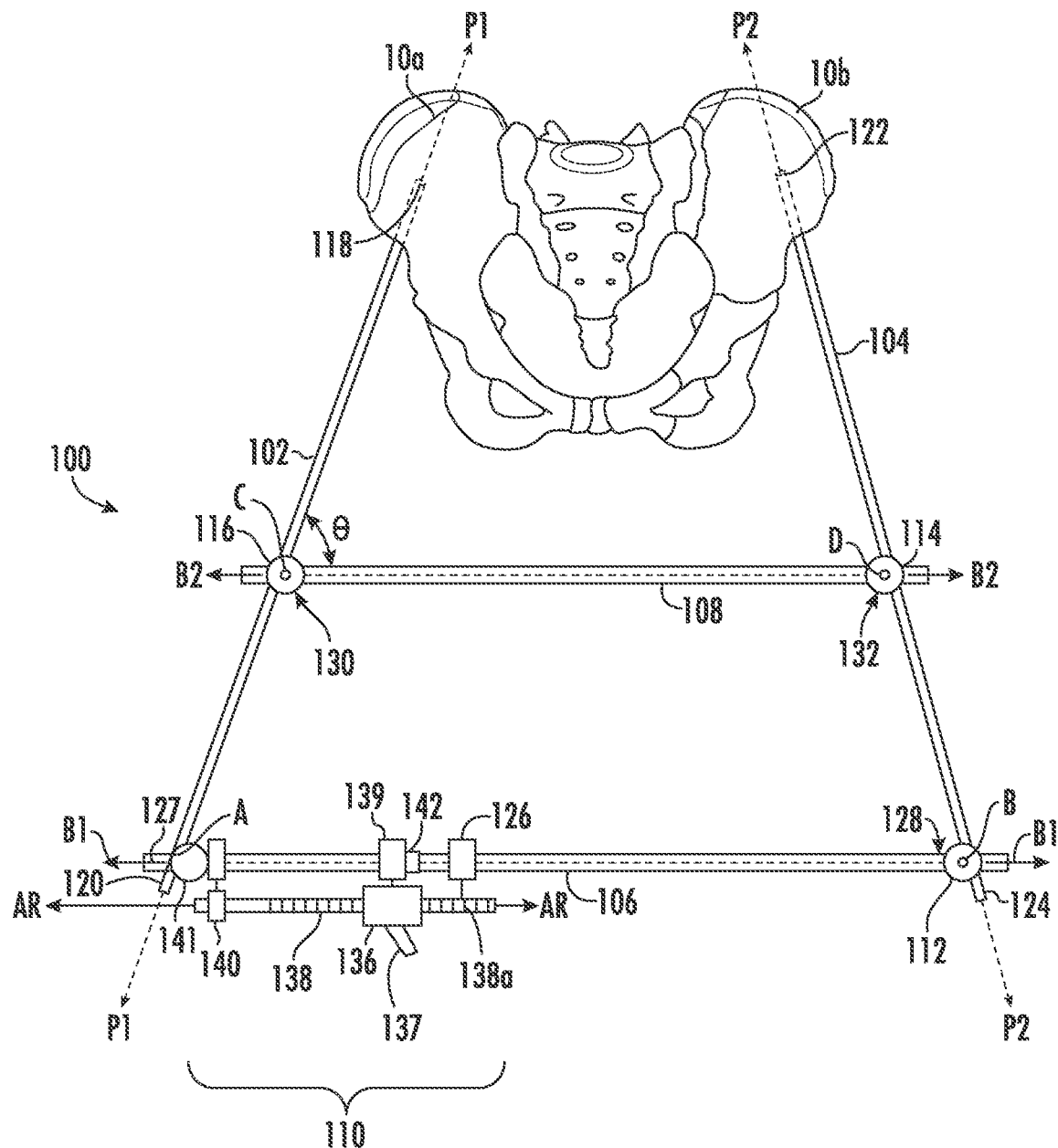
FIG. 1 shows a front perspective view of an external fixation device according to one implementation.

For example, in the implementation shown in FIG. 1, an external fixation device 100 for posterior pelvic compression includes a first pin 102, a second pin 104, a first bar 106, a second bar 108, a distractor 110, a first fixed clamp 112, a second fixed clamp 114, and a hinge clamp 116. The first pin 102 has a first end 118 and a second end 120 and an axis P1-P1 extending through the first 118 and second ends 120, and the first end 118 is disposable into a first iliac wing 10a of a patient. The second pin 104 has a first end 122 and a second end 124 and axis P2-P2 extending through the first 122 and second ends 124 of the second pin 104, and the first end 122 of the second pin 104 is disposable into a second iliac wing 10b of the patient. In the implementation shown in FIG. 1, the first ends 118, 122 of the first 102 and second pins 104, respectively, are threaded for engaging the iliac wings 10a, 10b, respectively. For example, the first 102 and second pins 104 are Schanz pins in some implementations.

The first bar 106 has a first end 127 and a second end 128 and an axis B1-B1 extending between the first 127 and second ends 128 of the first bar 106. The first bar 106 is coupled to the first pin 102 at a first region A of the first pin 102 and adjacent the first end 127 of the first bar 106, and the first bar 106 is coupled to the second pin 104 at a second region B of the second pin 104 and adjacent the second end 128 of the first bar 106.

The second bar 108 has a first end 130 and a second end 132 and an axis B2-B2 extending between the first 130 and second ends 132 of the second bar 108, and the second bar 108 is coupled to the first pin 102 at a third region C of the first pin 102 and adjacent the first end 130 of the second bar 108. The second bar 108 is coupled to the second pin 104 at a fourth region D of the second pin 104 and adjacent the second end 132 of the second bar 108. The third region C is disposed between the first end 118 of the first pin 102 and the first region A, and the fourth region D is disposed between the first end 122 of the second pin 104 and the second region B.

The distractor 110 couples the first bar 106 and the first pin 102. The distractor 110 is coupled to the first region A of the first pin 102 and the first bar 106 adjacent the first end 127 of the first bar 106. Actuation of the distractor 110 causes the first region A of the first pin 102 to move along the axis B1-B1 of the first bar 106. The first fixed clamp 112 couples the first bar 106 and the second pin 104 at the second region B, and the second fixed clamp 114 couples the second bar 108 and the second pin 104 at the fourth region D. As shown in the implementation of FIG. 1, the distractor 110 is fixedly coupled to the first region A of the first pin 102.

In the implementation shown in FIG. 1, the distractor 110 is a known distractor, such as the JET X distractor from Smith and Nephew. The distractor 110 includes an actuation bar 138, an actuation housing 136 having an actuation device 137, a first distractor clamp 142 that is fixedly coupled to the first bar 106, a second distractor clamp 140 that is fixedly coupled to the actuation bar 138 and slidably coupled to the first bar 106, a third distractor clamp 141 that is slidably coupled to the first bar 106 and fixedly coupled to the first pin 102, and fourth distractor clamp 139 that is fixedly coupled to the actuation housing 136 and is slidably coupled to the first bar 106. The second distractor clamp 140 is slidably coupled to the first bar 106 between the third distractor clamp 141 and the fourth distractor clamp 139. An axis AR-AR of the actuation bar 138 is parallel and spaced apart from the axis B1-B1. Actuation of the actuation device 137 causes the actuator bar 138 to move axially along the AR-AR axis relative to the actuation housing 136. The fourth distractor clamp 139 is fixedly coupled to the housing 136 and abuts the first distractor clamp 142 that is fixedly coupled to the first bar 106 such that axial movement of the housing 136 relative to the actuation bar 138 urges the third distractor clamp 141 away from the housing 136, which causes the clamp 140 to urge the third distractor clamp 141 axially along the B1-B1 axis of the first bar 106. Movement of the third distractor clamp 141, which is fixedly coupled to the first pin 102 adjacent the second end 120 of the pin 102, causes the ends 118, 120 of the first pin 102 to pivot about hinge axis of the hinge clamp 116, which is described below. In the implementation shown, the actuator bar 138 defines a plurality of teeth 138a or notches spaced apart axially along a portion of the bar 138, and the actuation device 137 is selectively movable to engage the teeth and urge the bar 138 to move along the AR-AR axis. For example, the actuation device 137 includes a handle (e.g., a spring biased handle) that is squeezed against the biasing force relative to (e.g., toward or away from) the housing 136 to urge a portion of the actuation device 137 (e.g., one or more protrusions) into contact with the teeth 138a of the actuation bar 138 to urge the actuation bar 138 along the axis AR-AR. Clamp 126 is fixedly coupled to the actuation bar 138 and slidably coupled to the first bar 106 to support that end of the actuation bar 138. In other implementations, the actuation device may include threads that extend radially inwardly into a channel defined by the actuation housing, and the actuation bar includes threads that extend radially outwardly from an outer surface of the actuation bar and engage the threads of the housing such that rotation of the threaded bar causes the threaded bar to move along its longitudinal axis depending on the direction of rotation.

A hinge clamp 116 couples the second bar 108 and the first pin 102 at the third region C of the first pin 102. The hinge clamp 116 allows an angle θ between the axis P1-P1 of the first pin 102 and the axis B2-B2 of the second bar 108 to change, such that the first pin 102 pivots about the hinge clamp 116. As discussed below in relation to FIG. 2, the hinge clamp 116 allows for one rotational degree of freedom while maintaining the axes P1-P1 and B2-B2 in parallel planes. Movement of the first region A of the first pin 102 along the axis B1-B1 of the first bar 106 urges the second end 120 of the first pin 102 away from the second end 128 of the second pin 104 along the axis B1-B1 and urges the first end 118 of the first pin 102 toward the first end 122 of the second pin 104, compressing a posterior portion of a pelvis of the patient. This movement provides a compressive force to the iliac wing 10a to which the first pin 102 is coupled in a direction toward the sacral bone and other iliac wing 10b. The first pin 102 is coupled to the iliac wing 10a closest to the injury.

Figure 2:
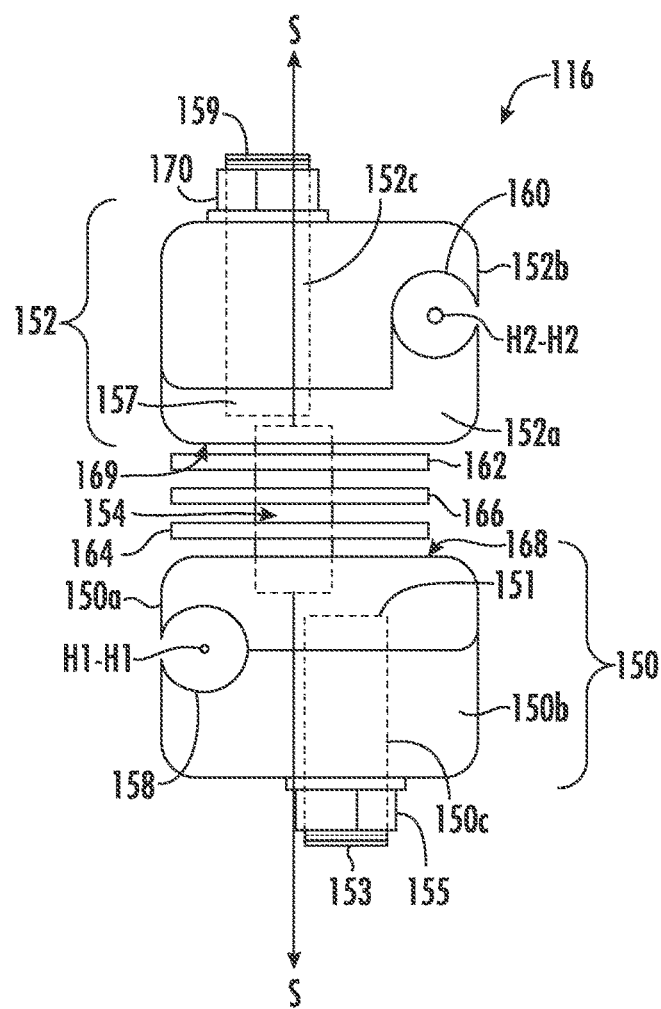
FIG. 2 shows a side view of a hinge clamp according to one implementation.

FIG. 2 illustrates the hinge clamp 116 shown in FIG. 1. The hinge clamp 116 comprises a pin portion 150 and a bar portion 152. The pin portion 150 and the bar portion 152 are coupled together via a shaft 154 that extends between the pin portion 150 and the bar portion 152, and the pin portion 150 and the bar portion 152 are spaced apart along an axis S-S of the shaft 154 and have a single rotational degree of freedom about the axis S-S. The pin portion 150 defines a pin opening 158 for fixedly receiving the first pin 102, and the bar portion 152 defines a bar opening 160 for fixedly receiving the second bar 108. A pin portion axis H1-H1 extends through the pin opening 158, and a bar portion axis H2-H2 extends through the bar opening 150. The axis P1-P1 of the first pin 102 is coincident with the pin portion axis H1-H1, and the axis B2-B2 of the second bar 108 is coincident with the bar portion axis H2-H2. A plane through which axis P1-P1 of the first pin 102 extends is parallel to the plane through which axis B2-B2 of the second bar 108 extends. Because the hinge clamp 116 allows for a single rotational degree of freedom about the axis S-S, the distractor 110 can be used to provide compressive force through the first end 118 of the first pin 102 without having to adjust additional clamps during the actuation process. In other implementations, the axes P1-P1 and H1-H1 are not coincident but are parallel and/or the axes B2-B2 and H2-H2 are not coincident but are parallel.

The pin portion 150 includes a first pin portion 150a and a second pin portion 150b that are coupled together via a shaft 150c. One end 151 of the shaft 150c is fixed to the first pin portion 150a and the other end 153 extends through and exterior of the second pin portion 150b. The pin portions 150a, 150b together define the pin opening 158. A nut 155 coupled to the exterior of the shaft 150c is rotated in a first direction about an axis of the shaft 150c to urge the first 150a and second portions 150b of the pin portion 150 toward each other and is rotated in a second direction (opposite of the first direction) about the axis of the shaft 150c to allow the first 150a and second portion 150b to move axially away from each other, allowing the pin 102 to be disposed within or removed from the pin opening 158.

Similarly, the bar portion 152 includes a first bar portion 152a and a second bar portion 152b that are coupled together via a shaft 152c. One end 157 of the shaft 152c is fixed to the first bar portion 152a and the other end 159 extends through an exterior of the second bar portion 152b. The bar portions 152a, 152b together define the bar opening 160. A nut 170 is coupled to the shaft 152c exterior of the bar portions 152a, 152b. The nut 170 is rotated in a first direction about an axis of the shaft 152c to urge the first 152a and second portions 152b of the bar portion 152 toward each other and is rotated in a second direction (opposite of the first direction) about the axis of the shaft 152c to allow the first 152a and second portion 152b to move axially away from each other, allowing the bar 108 to be disposed within or removed from the bar opening 160.

The hinge clamp 116 further includes a first washer 162, a second washer 164, and a spacer 166 disposed between facing surfaces 168, 170 of the pin 150 and bar portions 152, respectively. The shaft 154 extends through openings defined in the washers 162, 164 and the spacer 166, and the washers 162, 164 and spacer 166 maintain a gap between the pin 150 and bar portions 154. The spacer 166 is axially disposed between the washers 162, 164. The washers 162, 164 and spacer 166 reduce the friction between the pin portion 150 and bar portion 152 as the pin portion 150 rotates relative to the bar portion 152, or vice versa. For example, the spacer 166 may include a disc.

Figure 5:
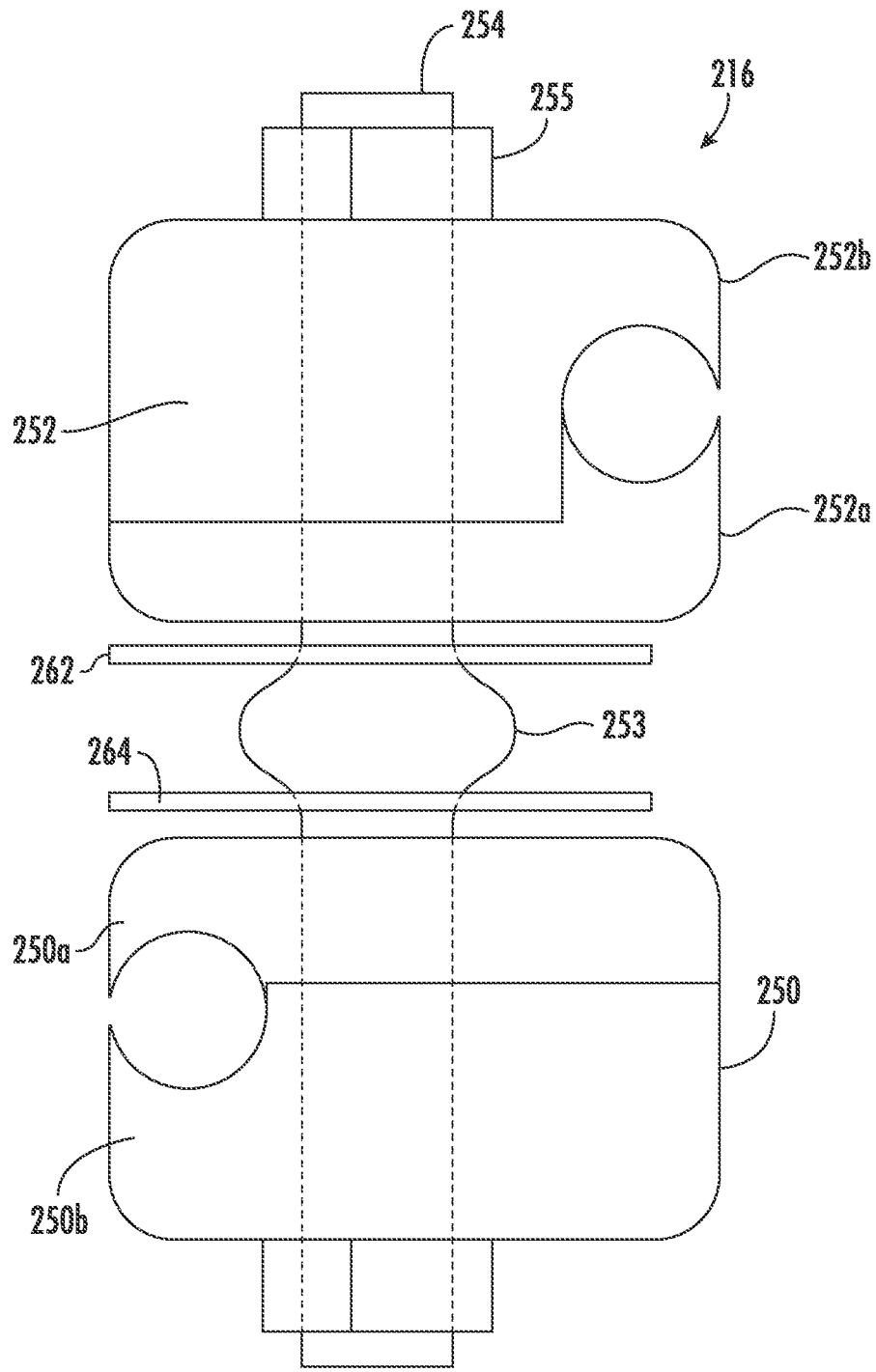
FIG. 5 shows a side view of a portion of a hinge clamp according to another implementation.

FIG. 5 illustrates another hinge clamp 216 according to one implementation. The hinge clamp 250 includes a single shaft 254 that extends through both bar portions 252a, 252b and both pin portions 250a, 250b, instead of having multiple shafts such as shown in FIG. 2 (e.g., shafts 154, 150c, and 152c). For example, the single shaft 254 may include a threaded portion at each end thereof and nuts 255 that threadingly engage each end to allow for urging the portions 250, 252 closer together or allowing them to move further apart. In addition, the shaft 254 includes an integrally formed radially extending protrusion 253 disposed between the portions 250, 252, and washers 262, 264 are disposed on each side of the protrusion 253. In other implementations, the protrusion 253 may not be integrally formed but may include a relatively rigid stopper disposed around the shaft 254. The washers 262, 264 may include a metal or plastic material that reduces the friction between the portions 150, 152 and the protrusion 253 when the portions 250, 252 are rotated relative to each other about the shaft 254.

In the implementation shown in FIG. 5, both ends of the shaft 254 are threaded, and nuts 255 are engaged about each end. However, in some implementations, only one of the nuts 255 may be rotated to allow the portions 250, 252 to move axially closer or apart. In addition, in other implementations, one end of the shaft 254 may include a head that abuts a distal end surface of portion 250 or 252, and the other end of the shaft 254 is threaded for threadingly engaging a nut 255.

Figure 3:
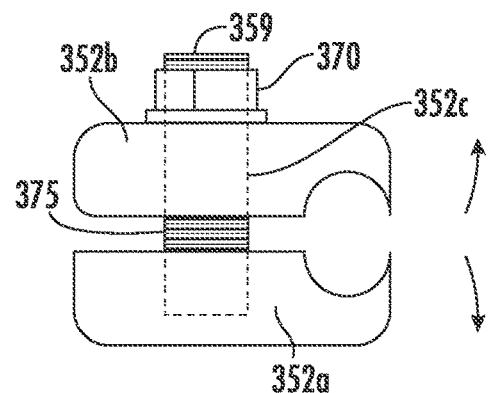
FIG. 3 shows a side view through a plane that includes a central axis of a portion of a hinge clamp according to another implementation.
Figure 4:
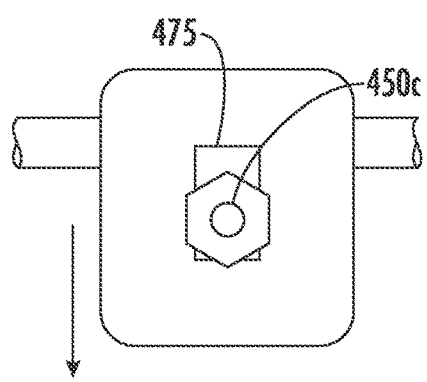
FIG. 4 shows an end view of a portion of a hinge clamp according to another implementation.

Other coupling mechanisms may be used for increasing and reducing the size of the pin and bar openings in the clamp in combination with the rotational couplings of the pin portion to the bar portion described above. For example, the coupling mechanism may include one of the clamps from the JET-X product series from Smith and Nephew, such as the pin-to-bar Quick Clamps. FIG. 3 illustrates a portion of one of the Quick Clamp clamps in which a spring 375 is disposed around the shaft 352c coupling the respective first 352a and second portions 352b of the pin portion or the bar portion. A nut 370 that is threadingly engaged around the free end 359 of the shaft 352c is turned in one direction to overcome the force of the spring 375 and urge the first 352a and second portions 352b toward each other and turned in another direction to allow the spring 375 to force the portions 352a, 352b apart. FIG. 4 illustrates another implementation of one of the Quick Clamp clamps in which a bolt 450c coupling the first and second portions of the pin portion or the bar portion is slidably disposed within a slot 475 defined in the first and second portions, such that sliding the bolt 450c in one direction allows the first and second portions to move apart and sliding in the opposite direction causes the first and second portions to move toward each other.

In other implementations (not shown), each facing surface 168, 169 of the pin 150 and bar portions 152, respectively, defines an annular race, and ball bearings are disposed within the annular races, which couples the portions 150, 152 and reduces the friction between the portions 150, 152 as they rotate relative to each other. In such an implementation, shaft 154 may not be included. In yet another implementation, ball bearings may be disposed radially (relative to the shaft 154) between the shaft 154 and each portion 150, 152. The ball bearings may be disposed within the portions 150, 152 and at least one washer or other spacer may be disposed between the facing surface 168, 169 to maintain the gap between the surfaces 168, 169. In other implementations, other types of suitable friction reducing mechanisms and/or spacers may be disposed between the portions 150, 152. For example, in some implementations, the one or more of the facing surfaces 168, 169 may be coated with a friction reducing material. In addition, as another example, spacers may be separately or integrally formed with one of the facing surfaces 168, 169. And, in yet another implementation, there may be no separate friction reducing mechanism and/or spacer between the portions 150, 152.

FIGS. 2-5 illustrate various implementation of hinge clamps, but other implementations may include any suitable rotational coupling that allows rotation of the pin portion relative to the bar portion about an axis of the rotational coupling, such as a pair of annular races and a plurality of ball bearing disposed between the races, a ball and socket joint, or a universal joint. In implementations in which the rotational coupling allows for more than one rotational degree of freedom of the pin portion relative to the bar portion, such as with a universal joint or a ball and socket joint, a fixed clamp may be disposed on the second bar such that the first pin is between the hinge clamp and the fixed clamp to prevent the hinge clamp from tilting the axis of the second bar. And, in further or alternative implementations, the device may also include a third bar that is fixedly coupled to the first bar and the second bar. The third bar prevents the first and second bars from twisting relative to each other. In other words, the axes of the first and second bars are maintained within one plane by the third bar.

An external fixation device, such as device 100 described above, may be assembled for applying posterior pelvic compression, and components of the device 100 may be anteriorly disposed, providing the patient clinical benefit while the device 100 is being used. A method of assembling the device 100 according to one implementation includes the following steps. First, a first end of a first pin is engaged into a first iliac wing of a patient, and a first end of a second pin is engaged into a second iliac wing of a patient. Then, a first bar is fixedly coupled to the second pin at a second region of the second pin and adjacent the second end of the second bar. And, a distractor is fixedly coupled to the first bar and the first pin. The distractor is coupled to a first region of the first pin and to the first bar adjacent the first end of the first bar. A second bar is hingedly coupled to the first pin and fixedly coupled to the second pin. After the bars and pins are coupled, the distractor is adjusted to move the first region of the first pin along the axis of the first bar, which causes an angle between the axis of the first pin and the axis of the second bar to change and causes the first end of the first pin to move the first iliac wing toward or away from the second iliac wing.

Figure 6:
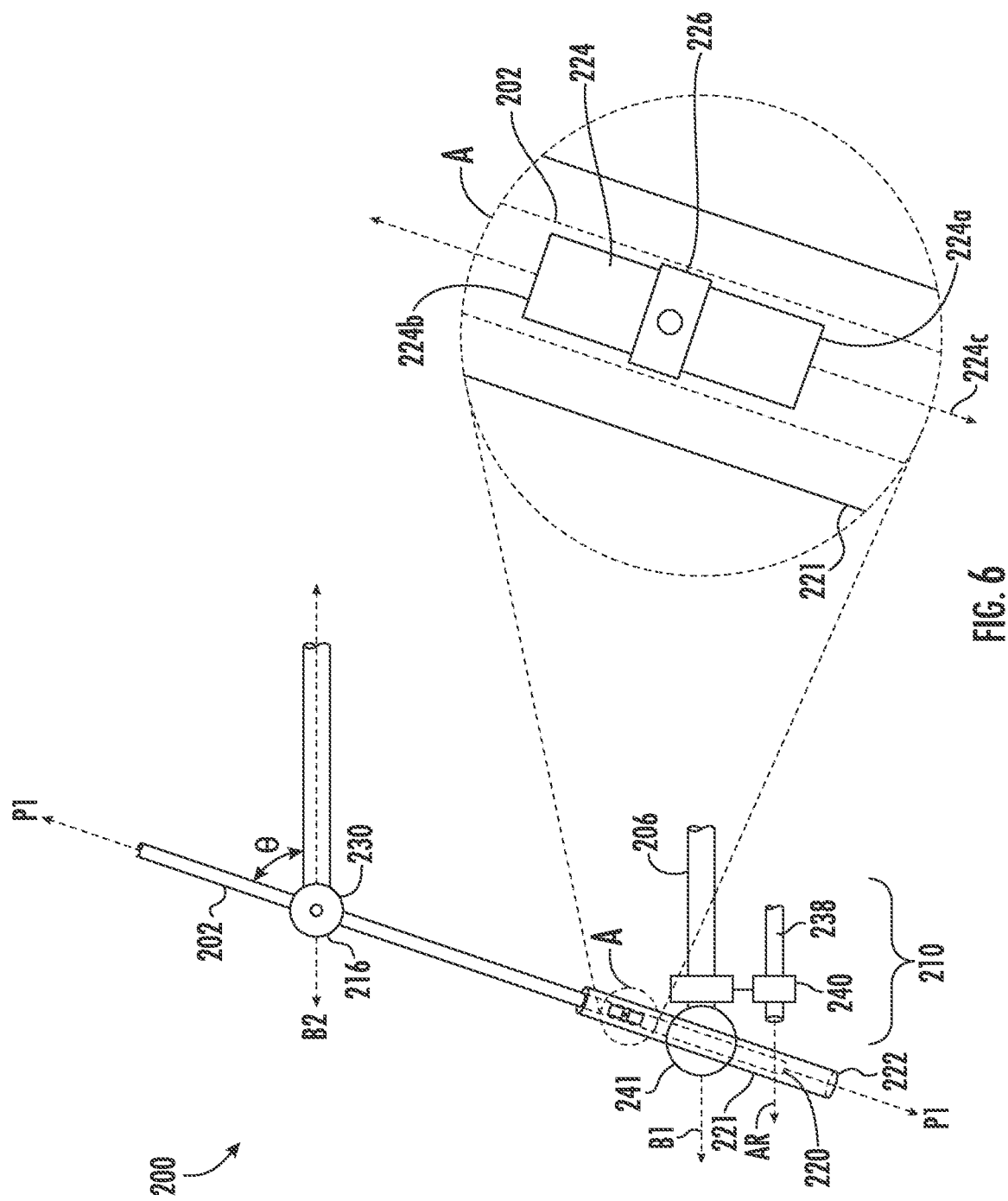
FIG. 6 illustrates a partial view of an external fixation device according to another implementation.

In the implementation shown in FIG. 1, the third distractor clamp 141 is slidably coupled to the first bar 106 and fixedly and directly coupled to the first pin 102. However, in other implementations, such as shown in FIG. 6, the third distractor clamp 241 may be fixedly and directly coupled to a sleeve 221 that is coupled to the first pin 202. The sleeve 221 defines a cavity extending axially through the sleeve 221, and the cavity has an inner diameter that is greater than an outer diameter of the first pin 202, which allows the sleeve 221 to slide axially along the pin 202. The sleeve 221 is disposed around the pin 202 adjacent the second end 220 of the pin 202. The third distractor clamp 241 of the distractor 210 is slidably coupled to the first bar 206, and the second distractor clamp 240, which is coupled to the first bar 206 and the actuation bar 238 of the distractor 210, abuts the clamp 241. In this implementation, an outer diameter of the sleeve 221 is the same as the outer diameter of the first bar 206, and the third distractor clamp 241 is a bar-to-bar clamp, such as the bar-to-bar Quick Clamp clamps from Smith and Nephew. However, the sleeve 221 may have a different diameter from the first bar 206, and other suitable clamps may be used for coupling the sleeve 221 and the first bar 206.

In addition, the sleeve 221 may be slidably or fixedly coupled to the first pin 202. In the implementation shown in FIG. 6, the sleeve 221 is slidably coupled to the first pin 202. As shown in close-up A of FIG. 6, the sleeve 221 defines a slot 224 that extends radially through a portion of the wall of the sleeve 221. The slot 224 has first end 224a and a second end 224b and an axis 224c that extends between the first end 224a and the second end 224b. The axis 224c is parallel with the axis P1-P1 of the first pin 202 when at least a portion of the first pin 202 is disposed in the cavity of the sleeve 221. A fastener 226, such as a bolt or pin, extends through the slot 224 and is fixedly coupled to the pin 202. As the sleeve 221 slides along the pin 202, the distance that the sleeve 221 can slide is limited by a length of the slot 224 from the first end 224a to the second end 224b.

The sleeve 221 acts as an extender for the first pin. For example, standard pins may not have sufficient length for larger patients that have more soft tissues covering the available length of the pin. Extending the length of the pin may also create more leverage and allow the device to provide more posterior compression when necessary. The dynamic compression provided by such implementations may also be helpful in reducing the posterior pelvis (e.g., as part of a definitive treatment effort) followed by internal fixation.

The terminology used herein is for the purpose of describing particular implementations only and is not intended to be limiting of the claims. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The descriptions of the various implementations have been presented for purposes of illustration and description but are not intended to be exhaustive or limiting in the form disclosed. Many modifications and variations will be apparent to those of ordinary skill in the art without departing from the scope and spirit of the claims. The implementation was chosen and described to best explain the principles of the claims and the practical application, and to enable others of ordinary skill in the art to understand the various implementations with various modifications as are suited to the particular use contemplated.

The invention claimed is:

1. An external fixation device for posterior pelvic compression, the device comprising:
a first pin having a first end and a second end and an axis extending through the first and second ends, the first end being disposable into a first iliac wing of a patient;
a second pin having a first end and a second end and axis extending through the first and second ends of the second pin, the first end of the second pin being disposable into a second iliac wing of the patient;
a first bar having a first end and a second end and an axis extending between the first and second ends of the first bar, wherein the first bar is coupled to the first pin at a first region of the first pin and adjacent the first end of the first bar, and the first bar is coupled to the second pin at a second region of the second pin and adjacent the second end of the first bar;
a second bar having a first end and a second end and an axis extending between the first and second ends of the second bar, wherein the second bar is coupled to the first pin at a third region of the first pin and adjacent the first end of the second bar, and the second bar is coupled to the second pin at a fourth region of the second pin and adjacent the second end of the second bar, wherein the third region is disposed between the first end of the first pin and the first region, and the fourth region is disposed between the first end of the second pin and the second region;
first and second fixed clamps, wherein the first fixed clamp couples the first bar and the second pin at the second region and the second fixed clamp couples the second bar and the second pin at the fourth region;
a distractor coupling the first bar and the first pin, the distractor being coupled to the first pin at the first region of the first pin;
a hinge clamp coupling the second bar and the first pin at the third region, the third region being between the first region and the first end of the first pin, wherein the hinge clamp is rotatable about a hinge axis, wherein the hinge axis is transverse to a first plane that includes the axis of the first pin and a second plane that includes the axis of the first bar such that an angle between the axis of the first pin and the axis of the second bar is able to change,
wherein actuation of the distractor urges the first region of the first pin along the axis of the first bar, which causes the first pin to pivot about the hinge axis of the hinge clamp.

2. The external fixation device of claim 1, wherein the distractor comprises an actuation bar having an actuation bar axis extending through the actuation bar, an actuation housing, an actuation device, a first distractor clamp, a second distractor clamp, a third distractor clamp, and a fourth distractor clamp, wherein:
the actuation device is operable for causing the actuation bar to slide along the actuation bar axis relative to the housing,
the first distractor clamp is fixedly coupled to the first bar,
the second distractor clamp is fixedly coupled to the actuation bar and slidably coupled to the first bar between the third distractor clamp and the fourth distractor clamp, the third distractor clamp is coupled to the first pin and slidably coupled to the first bar, the fourth distractor clamp is fixedly coupled to the actuation housing and slidably coupled to the first bar between the second distractor clamp and the first distractor clamp, when the actuation device is actuated, a portion of the actuation bar that is coupled to the third distractor clamp slides along the actuation bar axis away from the actuation housing, the fourth distractor clamp is urged into abutment with the first distractor clamp, and the second distractor clamp urges the third distractor clamp and the second end of the first pin in a direction away from the actuation housing, and the first end of the first pin is moved toward the first end of the second pin.

3. The external fixation device of claim 2, wherein the actuation bar defines axially spaced notches, and the actuation device comprises a trigger that is alternately pulled and released to engage the notches upon actuation of the actuation device to push the actuation bar along the actuation bar axis.

4. The external fixation device of claim 2, wherein the actuation bar axis is parallel to an axis of the first bar.

5. The external fixation device of claim 2, wherein an elongated sleeve is disposed around and coupled to at least a portion of the first pin adjacent the second end of the first pin, and the third distractor clamp is fixedly coupled to the elongated sleeve.

6. The external fixation device of claim 5, wherein the elongated sleeve is slidably coupled to the first pin.

7. The external fixation device of claim 6, wherein the elongated sleeve defines a slot extending radially through a wall of the sleeve, the slot having an axis that is parallel to the axis of the first pin, and the device further comprises a fastener that extends through the slot and engages the first pin, wherein the slot limits a length that the sleeve can slide relative to the first pin.

8. The external fixation device of claim 1, wherein the distractor is fixedly coupled to the first region of the first pin.

9. The external fixation device of claim 1, wherein the hinge clamp comprises a pin portion and a bar portion, the pin portion and the bar portion are coupled together via a rotational coupling that extends between the pin portion and the bar portion, and the pin portion and the bar portion are independently rotatable relative to each other about an axis of the rotational coupling, wherein the pin portion defines a pin opening that receives the first pin, and the bar portion defines a bar opening that receives the second bar, wherein the rotational coupling allows for one rotational degree of freedom while maintaining the axis of the first pin and the axis of the second bar in parallel planes.

10. The external fixation device of claim 9, wherein the rotational coupling comprises a shaft, and the hinge clamp further includes at least one washer disposed between facing surfaces of the pin and bar portions, the shaft extending through an opening defined in the at least one washer.

11. The external fixation device of claim 10, wherein the at least one washer includes a first washer and a second washer, and the hinge clamp further includes a spacer disposed between the first and second washers.

12. The external fixation device of claim 11, wherein the spacer comprises an integrally formed protrusion that extends radially outwardly from an outer surface of the shaft.

13. The external fixation device of claim 11, wherein the spacer comprises a separately formed disc disposed around the shaft that maintains a gap between the washers.

14. The external fixation device of claim 11, wherein the shaft comprises a threaded portion adjacent a first end of the shaft, and at least a portion of the threaded portion extends distally of one of the bar portion or the pin portion, and the hinge clamp further comprises a nut that threadingly engages the threaded portion to urge the pin and bar portions axially toward or away from each other.

15. The external fixation device of claim 14, wherein the shaft includes a head adjacent a second end of the shaft, the head being disposed adjacent a distal surface of the other of the pin portion or the bar portion.

16. The external fixation device of claim 14, wherein the threaded portion is a first threaded portion and the nut is a first nut, and the shaft comprises a second threaded portion adjacent a second end of the shaft, and at least a portion of the second threaded portion extends distally of the other of the pin or bar portion, and the hinge clamp comprises a second nut that threadingly engages the threaded portion to urge the pin and bar portions axially toward or away from each other.

17. The external fixation device of claim 1, wherein the first ends of the first and second pins are threaded.

18. The external fixation device of claim 17, wherein the first and second pins are Schanz pins.

19. A method of assembling an external fixation device for applying pelvic compression, the method comprising:

engaging a first end of a first pin into a first iliac wing of a patient, the first pin having a second end opposite the first end and an axis extending through the first and second ends;

engaging a first end of a second pin into a second iliac wing of a patient, the second pin having a second end opposite the first end of the second pin and an axis extending through the first and second ends of the second pin;

coupling a first bar to the second pin, wherein the first bar includes a first end and a second end and an axis extending between the first and second ends of the first bar, wherein the first bar is fixedly coupled to the second pin at a second region of the second pin and adjacent the second end of the second bar;

coupling a distractor to the first bar and the first pin, the distractor being coupled to a first region of the first pin and to the first bar adjacent the first end of the first bar, wherein the distractor is actuatable for moving the first region of the first bar;

coupling a second bar to the first pin and the second pin, the second bar having a first end and a second end and an axis extending between the first and second ends of the second bar, wherein the second bar is hingedly coupled to the first pin at a third region of the first pin and adjacent the first end of the second bar, and the second bar is fixedly coupled to the second pin at a fourth region of the second pin and adjacent the second end of the second bar, and wherein the third region is disposed between the first end of the first pin and the first region, and the fourth region is disposed between the first end of the second pin and the second region; and actuating the distractor to cause the first region of the first pin to move along the axis of the first bar, which causes the first pin to pivot about the hinged coupling relative to the second bar.

* * * * *